(12) United States Patent
Rimington et al.

(10) Patent No.: US 7,662,807 B2
(45) Date of Patent: Feb. 16, 2010

(54) SULPHONATED MESO-TETRAPHENYL CHLORINS

(75) Inventors: Claude Rimington, Son (NO); Greta Rimington, legal representative, Son (NO); Kristian Berg, Heggedal (NO); Diem Thuy Thi Tran, Oslo (NO); Pal Kristian Selbo, Oslo (NO)

(73) Assignee: The Norwegian Radium Hospital Research Foundation (NO)

( * ) Notice: Subject to any disclaimer, the term of this patent is extended or adjusted under 35 U.S.C. 154(b) by 1025 days.

(21) Appl. No.: 10/489,559

(22) PCT Filed: Aug. 30, 2002

(86) PCT No.: PCT/GB02/03973

§ 371 (c)(1),
(2), (4) Date: Mar. 24, 2005

(87) PCT Pub. No.: WO03/020309

PCT Pub. Date: Mar. 13, 2003

(65) Prior Publication Data

US 2006/0052433 A1    Mar. 9, 2006

(30) Foreign Application Priority Data

Aug. 30, 2001 (GB) .................................. 0121023.6

(51) Int. Cl.
*C07D 487/22* (2006.01)
*C07B 47/00* (2006.01)
*A01N 55/02* (2006.01)

(52) U.S. Cl. ........................................ 514/183; 540/145

(58) Field of Classification Search ............... 540/145; 514/183
See application file for complete search history.

(56) References Cited

FOREIGN PATENT DOCUMENTS

| JP | 05253466 | * | 3/1992 |
|---|---|---|---|
| JP | 2000007693 | | 1/2000 |
| WO | 8901630 | | 2/1989 |
| WO | 9607432 | | 3/1996 |
| WO | 9830242 | | 7/1998 |
| WO | 0054802 | | 9/2000 |

OTHER PUBLICATIONS

Woodburn et al., Int. J. Biochem. Cell Biol. vol. 27, No. 5, pp. 499-506, 1995.*
Choi et al., "Counterion-Dependent Excitonic Spectra . . . " J'nal of ACS' 2003, 125(3), 810-820.*
Pascu et al., "Photodynamic therapy studies . . . ", Proceedings of SPIE, (1999), 4166, 138-148.*
Hall et al., "Hard and soft porphyrins . . . ", J'nal of Porphyrins and Phthalocyanines (2000), 4(3), 256-260.*
Woodburn et al., "Effect of density-gradients on the binding of photosensitizing agents . . . " Int'l J'nal of Biochemistry & Cell Biology, 1995 27(5), 499-506.*
Human Gene Therapy 11:869-880 (Apr. 10, 2000).
J. Chem. Soc. 1957, 3461-3469.
International Search Report for PCT/GB02/03973 dated May 8, 2003.
Photochemistry and Photobiology, 2001, 74(2), 303-310.
Int. J. Cancer: 87, 853-859 (2000).
Photochemistry and Photobiology 1976, vol. 23, 337-341.
J. Chem. Soc. Perkin Trans. 2, 1999, 325-328.
Biochem J. (1989) 261, 277-280.
Br. J. Cancer (1991) 64, 1116-1120.
J. Org. Chem. 1962, 27, 3060-3062.
J. Chem. Soc. 1957, 733-739.
J. Am. Chem. Soc. 1969, 91(26), 7485-7489.
J. Chemical Physics 1955, 23(6), 1068-1078.
Cancer Research 1999, 59, 1180-1183.

(Continued)

*Primary Examiner*—James O. Wilson
*Assistant Examiner*—Paul V. Ward
(74) *Attorney, Agent, or Firm*—Cantor Colburn LLP

(57) ABSTRACT

The present invention provides photosensitizing agents obtained by reducing a single double bond in the porphyrin macrocycle of a sulphonated meso-tetraphenylporphyrin, preferably a disulphonated meso-tetraphenylporphyrin such as $TPPS_{2a}$. The resulting sulphonated meso-tetraphenyl chlorins include compounds of formula (I) (wherein X is —$SO_3H$; n, p, q and r are each independently 0 or 1; and the sum of n, p, q and r is an integer from 1 to 4, preferably at least 2, e.g. 2 or 4) isomers and isomer mixtures thereof. The compounds of the invention and their pharmaceutically acceptable salts find particular use as photosensitizing agents in the photochemical internalization of molecules and in photodynamic therapy.

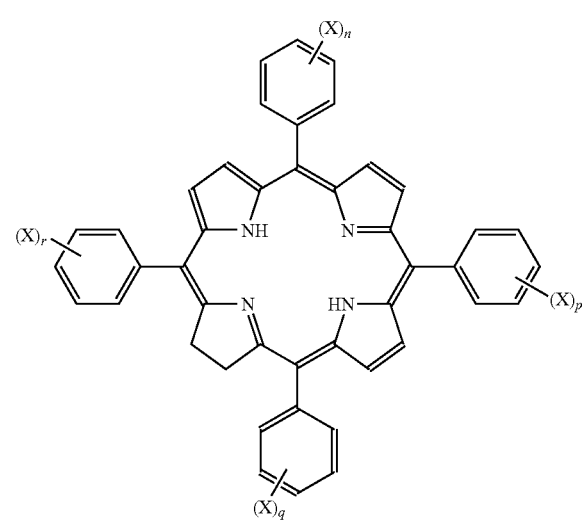

(I)

10 Claims, 8 Drawing Sheets

OTHER PUBLICATIONS

Ravindra K. Pandey et al.; Alkyl Ether Analogs of Chlorophyll-a Derivatives: Part 1. Synthesis, Photophysical Properties and Photodynamic Efficacy; Photochemistry and Photobiology; 1996; 64(1), pp. 194-204.

Barbara W. Henderson et al.; An in vivo Quantitative Structure-Activity Relationship for a Congeneric Series of Pyropheophorbide Derivatives as Photosensitizers for Photodynamic Therapy; Cancer Research; 1997; 57(18); pp. 4000-4007.

Hungarian Patent Office Novelty Search Report; Application No. P0401434; Dated Apr. 1, 2008; only 1 page.

Kessel, et al. "Promotion of porphyrin cytotoxicity by ultrasound"; Optical Methods for Tumor Treatment and Detection, vol. 1645, 1992, pp. 82-90.

MacDonald, et al. "Subcellular Localization Patterns and Their Relationship to Photodynamic Activity of Pyropheophorbide-a Derivatives"; Photochemistry and Photobiology, vol. 70(5), 1999, pp. 789-797.

Berg, et al. "Cellular Uptake and Relative Efficiency in Cell Inactivation by Photoactivated Sulfonated meso-Tetraphenylporphines"; Photochemistry and Photobiology, vol. 52, No. 4, 1990, pp. 775-781.

Noodt, et al. "Different apoptotic pathways are induced from various intracellular sites by tetraphenylporphyrins and light"; British Journal of Cancer, vol. 79, 1999, pp. 72-81.

JP Publication No. 2000-007693; filed Jan. 22, 2000; Title: Chlorin Derivative; Abstract Only; 1 page.

Berg, et al; "Intracellular Localization of Sulfonated meso-Tetraphenylporphines in a Human Carcinoma Cell Line"; Photochemistry and Photobiology; 52; pp. 481-487; (1990).

Berg, et al; "Lysosomes as Photochemical Targets"; Int. J. Cancer; 59; pp. 814-822; (1994).

\* cited by examiner

SULPHONATED MESO-TETRAPHENYL CHLORINS

CROSS-REFERENCE TO RELATED APPLICATIONS

This application is a 371 of PCT/GB02/03973 filed Aug. 30, 2002, which claims the benefit of the filing date of Aug. 30, 2001 to Great Britain application No. 0121023.6 under provisions of 35 U.S.C. 119 and the International Convention for the protection of Industrial Property.

The present invention relates to novel photosensitizing agents and their use in photochemical internalization of molecules and in photodynamic therapy.

A wide range of photosensitizing agents are known in the art. Upon exposure to light these may become toxic or may release toxic substances such as singlet oxygen or other oxidising radicals which are damaging to cellular material or biomolecules, including the membranes of cells and cell structures, and such cellular or membrane damage may eventually kill the cells. These cytotoxic effects have been used in the treatment of various abnormalities or disorders, including neoplastic diseases. Such treatment is known as photodynamic therapy (PDT) and involves the administration of photosensitizing (photochemotherapeutic) agents to the affected area of the body, followed by exposure to activating light in order to activate the photosensitizing agents and convert them into cytotoxic form, whereby the affected cells are killed or their proliferative potential diminished.

More recently, the photodynamic effect has been proposed as a tool for introducing otherwise membrane-impermeable molecules into the cytosol of a cell in such a way that this does not necessarily result in cell destruction or death. In this method, known as "photochemical internalization" or PCI, the molecule to be internalized or transferred is applied to the cells in combination with a photosensitizing agent. Exposure of the cells to light of a suitable wavelength activates the photosensitizing compound which in turn leads to disruption of the intracellular compartment membranes and the subsequent release of the molecule into the cytosol.

Photosensitizing agents may exert their effects by a variety of mechanisms, directly or indirectly. Thus for example, certain photosensitizers become directly toxic when activated by light, whereas others act to generate toxic species, e.g. oxidising agents such as singlet oxygen or oxygen-derived free radicals, which are extremely destructive to cellular material and biomolecules such as lipids, proteins and nucleic acids.

Known photosensitizing agents include, for example, the psoralens, the porphyrins, the chlorins and the phthalocyanines. Porphyrin photosensitizers act indirectly by generation of toxic oxygen species, and are regarded as particularly favourable candidates for PDT. Porphyrins are naturally occurring precursors in the synthesis of heme. In particular, heme is produced when iron ($Fe^{2+}$) is incorporated in protoporphyrin IX (PpIX) by the action of the enzyme ferrochelatase. PpIX is an extremely potent photosensitizer, whereas heme has no photosensitizing effect.

A variety of porphyrin-based or porphyrin-related photosensitizers are known in the art and are described in the literature. Examples of such agents include Photofrin® which has recently been approved for use as a photosensitizer in treating certain cancers. However, since Photofrin® must be administered parenterally (e.g. intravenously), this has the disadvantage that this causes prolonged photosensitization of the skin which may last for several weeks. Since Photofrin® consists of large oligomers of porphyrin, it also does not readily penetrate the skin when applied topically. Similar problems exist with other porphyrin-based photosensitizers such as the so-called "hematoporphyrin derivative" (HpD) which has also been reported for use in cancer photochemotherapy.

More recently, sulphonated meso-tetraphenyl porphyrins ($TPPS_ns$), such as the disulphonated meso-tetraphenylporphines $TPPS_{2a}$ and $TPPS_{2o}$, and the tetrasulphonated meso-tetraphenylphorphine $TPPS_4$, have been investigated for use as photosensitizing agents and have been found to possess some important advantages relative to HpD and Photofrin®. In particular, they have a high tumor:normal tissue ratio and are therefore of interest for use in photochemotherapy (Peng et al., Cancer Lett. 36: 1-10, 1987; Evensen et al., Photodynamic therapy of tumors and other diseases (Ed. G. Jori and C. Perria), p. 215-219, Libreria Prongetto Publ., Padova; and Winkelman, Cancer Res. 22: 589-596, 1962). $TPPS_{2a}$ has also recently been found to be suitable for use as a photosensitizer for photochemical internalization of macromolecules (Berg et al., Cancer Res. 59: 1180-1183, 1999; Høgset et al., Hum. Gene Ther. 11: 869-880, 2000; and Selbo et al., Int. J. Cancer 87: 853-859, 2000).

However, the main disadvantage in using $TPPS_{2a}$ for clinical purposes is its low absorbance of red light. Indeed, a major limitation to the clinical use of all known porphyrin derivatives is that the longest wavelength of light to which these respond has a relatively low absorbance lying at about 620-630 nm. At such wavelengths light is only able to penetrate a short distance into living tissues and is consequently unable to reach deep-seated cells or tissues, e.g. tumor cells. It is therefore desirable to find alternative tetrapyrrole compounds which still possess the advantageous properties of known porphyrin-based photosensitizers, but which also exhibit higher light absorption at longer wavelengths where tissue penetration is greater.

The present invention seeks to address this need and in particular aims to provide agents which have an enhanced photosensitizing effect over those porphyrin-based compounds described in the prior art.

It has now been found that reduction of one double bond in the porphyrin macrocycle of a sulphonated meso-tetraphenylporphyrin (e.g. a disulphonated meso-tetraphenylporphyrin) results in compounds having surprisingly enhanced photosensitizing properties. In particular, such compounds have improved spectral properties compared to the corresponding porphyrins and have been found to exhibit an unexpected increase in the extinction coefficient on exposure to red light, e.g. to light having a wavelength in the region of from 630 to 680 nm. Such compounds are thus considered to be particularly suitable for use not only in conventional methods of photodynamic therapy but also in methods of photochemical internalization of macromolecules.

Viewed from one aspect the invention thus provides a photosensitizing agent which comprises a sulphonated meso-tetraphenyl chlorin, e.g. a disulphonated meso-tetraphenyl chlorine or a pharmaceutically acceptable salt thereof. In such compounds at least one of the four phenyl rings will typically carry 1, 2 or 3, preferably 1, sulphonate group. Preferred compounds in accordance with the invention include those in which two phenyl rings are each substituted by a single sulphonate group.

Viewed from a further aspect the invention provides a photosensitizing agent obtainable by reducing one double bond in the porphyrin macrocycle of a sulphonated meso-tetraphenylporphyrin, in particular an agent obtainable by reducing one double bond in the porphyrin macrocycle of a disulphonated meso-tetraphenylporphyrin such as $TPPS_{2a}$.

Pharmaceutically acceptable salts of such compounds form a further aspect of the invention.

Examples of photosensitizing agents in accordance with the invention include those compounds of formula I:

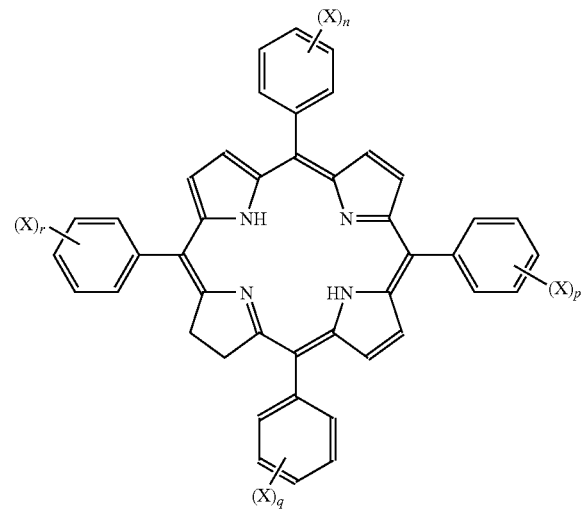

(I)

(wherein
X is —SO$_3$H;
n, p, q and r are each independently 0 or 1; and the sum of n, p, q and r is an integer from 1 to 4, preferably at least 2, e.g. 2 or 4) and pharmaceutically acceptable salts thereof.

Isomeric forms of the compounds of formula I, for example those in which the reduced double bond is located in any one of the three remaining pyrrole rings, are also considered to form part of the invention. Any isomeric mixture comprising at least one compound of formula I or an isomer thereof is considered to form part of the invention. Examples of isomers of compounds of formula I which are particularly suitable for use in the invention include the following compounds of formulae Ia-Ic:

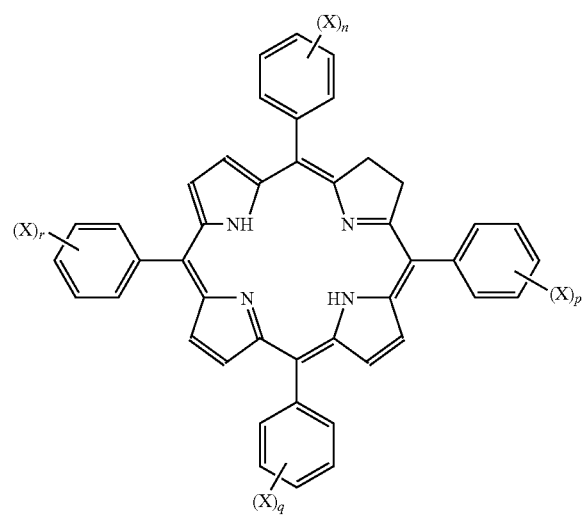

Ia

Ib

Ic (wherein
X, n, p, q and r are as hereinbefore defined).

In the compounds of formulae I, Ia, Ib and Ic, where any one of n, p, q and r is 1 this signifies the presence of a single sulphonate group attached to the phenyl ring at any ring position (i.e. ortho-, meta- or para-). In those cases where more than one sulphonate group is present, these may be present at the same or different ring positions within each phenyl ring. Preferably, these will be present in the same ring positions, most preferably in the meta- or para-position. Where any of n, p, q and r is zero, this signifies the absence of any ring substituents, i.e. unsubstituted phenyl.

Particularly preferred compounds of formulae I, Ia, Ib and Ic are those in which the sum of n, p, q and r is 2. Most preferred are those compounds in which the substituted phenyl rings are situated adjacent to each other, e.g. adjacent to the reduced pyrrole ring, i.e. in which n=0, p=0, q=1 and r=1 in the compounds of formula I. Alternative preferred compounds of formulae I, Ia, Ib and Ic include those in which the sum of n, p, q and r is 2 and the substituted phenyl rings are situated opposite each other, for example compounds of formula I in which n=0, p=1, q=0 and r=1.

Independently, in each phenyl ring the sulphonated group X may be present in the ortho-, meta- or para-position. Preferably, this will be present in the meta- or para-position, most preferably the para-position. Preferred compounds in accordance with the invention include the compounds of formula II:

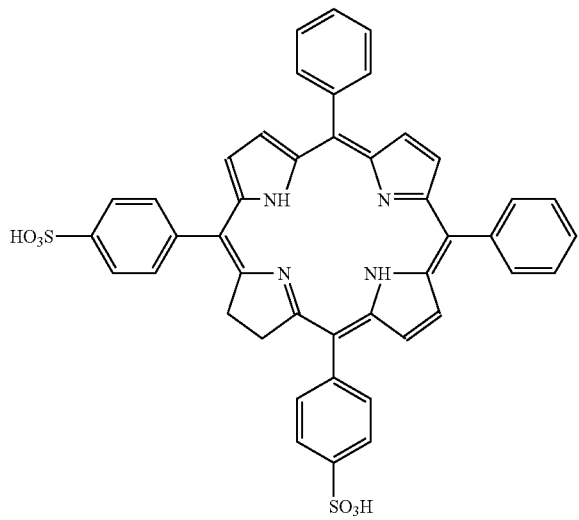

II

Isomeric forms of the compounds of formula II, for example those in which the reduced double bond is located in any one of the three remaining pyrrole rings are also considered to form part of the invention. Any isomeric mixture comprising at least one compound of formula II, and isomers thereof, is considered to form part of the invention.

A particularly preferred compound of formula II is that in which the two substituted phenyl rings are adjacent to the reduced double bond.

The compounds of the invention may be prepared using standard processes and procedures well-known in the art. Most conveniently these may be prepared by reduction of the corresponding porphyrin.

In a further aspect, the present invention thus provides a process for preparing the compounds of the invention, said process comprising at least one of the following steps:

(a) reducing a sulphonated tetraphenyl porphyrin or an iron chelate complex thereof, for example reducing a tetraphenyl porphyrin of formula III:

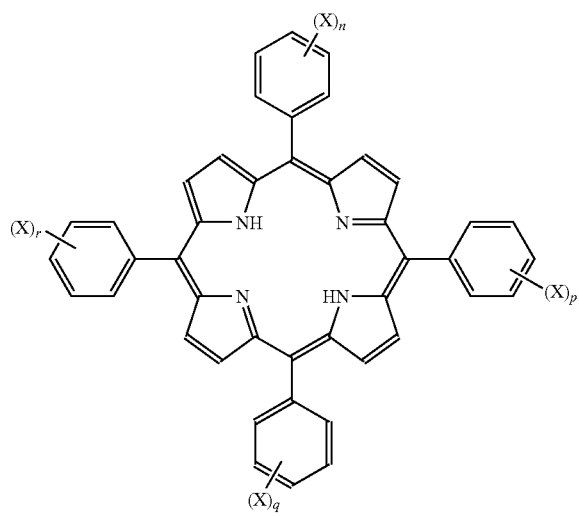

(III)

or an iron chelate complex thereof (wherein X, n, p, q and r are as hereinbefore defined);

(b) if desired, separating the mixture of compounds formed in step (a) by conventional separating techniques; and (c) converting a compound formed in step (a) or step (b), for example a compound of formula I, into a pharmaceutically acceptable salt thereof.

In step (a) the porphyrin compound used as a starting material is commercially available, or may be obtained using methods known in the art. Sulphonated porphyrins, including $TPPS_{2a}$ (disulphonated tetraphenylporphine), for example, are available from Porphyrin Products, Logan, Utah, USA.

Chemical transformation of the porphyrin compound of formula III into the corresponding chlorin in step (a) may be achieved chemically in several different ways, for example using p-toluenesulfonylhydrazine as a diimide precursor in the reduction of the free base porphyrin (see, for example, Whitlock et al., J. Am. Chem. Soc. 91: 7485-7489, 1969). Alternatively, production of the desired chlorin may be effected by reduction of the corresponding iron-porphyrin, for example with sodium in boiling isoamyl alcohol (see Eisner, J. Chem. Soc. 3461-3469, 1957; and Eisner et al., J. Chem. Soc. 733-739, 1957).

Particularly preferred for use in the preparation of the compounds of the invention is the photochemical reduction of porphyrins, optionally in the presence of a tertiary amine base. For example, a free base porphyrin may be photoreduced to chlorin in the presence of an amine, especially a tertiary amine (see, for example, Harel et al. Photochem. Photobiol. 23: 337-341, 1976).

Reduction of the porphyrin molecule in the presence of diimide may induce formation of bacteriochlorins by reducing two double bonds in the porphyrin macrocycle. A photoreduction process using an amine, particularly preferably a tertiary amine, is therefore preferred for use in the production of the desired chlorin compounds of the invention. Examples of suitable tertiary amines for use in such a process include triethylamine (TEA), N-methyl pyrrolidone, tri-n-butylamine, trioctylamine, etc., and reduction will generally be effected in the presence of visible light (i.e. photoreduction).

Photochemical reduction of a porphyrin may conveniently be carried out in a solvent or mixture of solvents such as benzene, pyridine, dimethylsulphoxide, etc. at temperatures in the range of from 10 to 30° C., preferably at ambient temperature (e.g. 20 to 25° C., especially 22° C.).

Photoreduction may be effected using light in the visible range, e.g. having a wavelength in the range of from 400 to 640 nm, preferably 500 to 640 nm, e.g. about 545±15 nm. Irradiation will generally be applied at a dose level of 1 to 50 $W/m^2$, e.g. about 15 $W/m^2$ for a period of time in the range of from 1 to 90 minutes, e.g. 5 to 40 minutes. The formation of any undesired bacteriochlorins can be reduced by limiting the period during which the porphyrin macrocycle is exposed to light. Methods for irradiation of the porphyrin, e.g. using lamps or lasers are well known in the art. Particularly suitable in this regard is a high pressure Xenon lamp or a tungsten iodine lamp such as those available from Philips. Typically, the reaction is conducted under anaerobic conditions, for example the mixture of starting materials and solvent may be saturated with nitrogen prior to light exposure and, optionally, also during light exposure.

The compounds of the invention may be present in the form of a mixture of isomers and may be used in this form. If desired, the compounds of the invention, e.g. those of formula I, may be separated into their isomers on the basis of their physical/chemical differences by methods known in the art, e.g. by chromatography and/or fractional crystallisation.

As mentioned above, the compounds of the invention may take the form of pharmaceutically acceptable salts. Such salts preferably are acid addition salts with physiologically acceptable organic or inorganic acids. Suitable acids include, for example, hydrochloric, hydrobromic, sulphuric, phosphoric, acetic, lactic, citric, tartaric, succinic, maleic, fumaric and ascorbic acids. Hydrophobic salts may also conveniently be produced by for example precipitation. Appropriate salts include for example acetate, bromide, chloride, citrate, hydrochloride, maleate, mesylate, nitrate, phosphate, sulphate, tartrate, oleate, stearate, tosylate, calcium, meglumine, potassium and sodium salts. Procedures for salt formation are conventional in the art.

As mentioned above, the compounds of the invention and their salts have valuable pharmacological properties, namely photosensitizing properties which renders them useful for photochemical internalization of macromolecules and as photochemotherapeutic agents.

In a further aspect the invention thus provides a pharmaceutical composition comprising a photosensitizing agent as herein described, e.g. a compound of formula I, or a pharmaceutically acceptable salt thereof, together with at least one pharmaceutical carrier or excipient.

In a yet further aspect the invention provides a photosensitizing agent as herein described, e.g. a compound of formula I, or a pharmaceutically acceptable salt thereof for use as a medicament, e.g. as a photosensitizing agent for use in a method of photochemical internalization, in photochemotherapy or diagnosis.

In a still further aspect, there is provided the use of a photosensitizing agent as herein described, e.g. a compound of formula I, or a pharmaceutically acceptable salt thereof, for the preparation of a therapeutic agent for use in a method of photochemical internalization, in photochemotherapy or diagnosis, in particular in a method of treating disorders or abnormalities of external or internal surfaces of the body which are responsive to photochemotherapy.

"Internalization" as used herein, refers to the cytosolic delivery of molecules and includes the step of release of molecules from intracellular/membrane bound compartments into the cytosol of the cells. The term "cell" is used herein to include all eukaryotic cells (including insect cells and fungal cells). Representative "cells" thus include all types of mammalian and non-mammalian animal cells, plant cells, insect cells, fungal cells and protozoa.

Methods for introducing molecules into the cytosol of living cells are useful tools for manipulating and studying biological processes. Of much interest are such methods in which the cells remain viable and/or functional following internalization. The use of a photosensitizing agent for introducing otherwise membrane-impermeable molecules into the cytosol of a cell in a manner which does not necessarily result in widespread cell destruction or cell death has been proposed, for example in WO 96/07432 and WO 00/54802. In this method, the molecule to be internalized and a photosensitizing compound are applied simultaneously or in sequence to the cells, upon which the photosensitizing compound and the molecule are endocytosed or in other ways translocated into endosomes, lysosomes or other intracellular membrane restricted compartments. The molecule to be translocated into intracellular compartments of the cells and the photosensitizing compound are applied to the cells together or sequentially and are taken up by the cell into intracellular compartments. The molecule to be internalized within the cell is released by exposure of the cells to light of suitable wavelengths to activate the photosensitizing compound which in turn leads to the disruption of the intracellular compartment membranes and the subsequent release of the molecule into the cytosol. This method, in which cells are exposed to light to release the molecule in question from the intracellular compartment in which it is contained by the action of a photosensitizing agent, is termed "photochemical internalization" or PCI.

In a still yet further aspect the present invention thus provides a method for introducing a molecule (i.e. a transfer molecule) into the cytosol of a cell either in vitro or in vivo, said method comprising contacting said cell with a photosensitizing agent as herein described, e.g. a compound of formula I, or a pharmaceutically acceptable salt thereof, contacting said cell with the molecule to be introduced and irradiating said cell with light of a wavelength effective to activate the photosensitizing agent, for example light having a wavelength in the range 300-800 nm.

The precise timing of the addition of the molecule to be transferred (i.e. the transfer molecule) and photosensitizing agent and timing of irradiation to achieve the above described effects needs to take into account various factors including the cells to be treated, the nature of the transfer molecules, the environment of the cells, whether the method is being carried out in vitro or in vivo, and whether administration is direct to the target tissue or at a distal site. Taking these considerations into account appropriate timings may readily be determined by those skilled in the art. Typically, the transfer molecule and the photosensitizing agent will be added to the cells prior to irradiation. For example, these may be applied either simultaneously or separately from 1 to 72 hours prior to irradiation, preferably 4 to 48, e.g. 4 to 24 hours prior to irradiation.

In certain cases, the transfer molecule will be administered simultaneously with the photosensitizing agent. In a further aspect the invention thus provides a pharmaceutical composition comprising a photosensitizing agent as herein described, together with a transfer molecule. A pharmaceutically acceptable carrier or excipient may additionally be present.

In a yet further aspect the invention provides a pharmaceutical composition comprising a photosensitizing agent as herein described, together with a transfer molecule, for use in therapy, e.g. for use in cancer or gene therapy.

In a still yet further aspect the invention provides the use of a photosensitizing agent as herein described and/or a transfer molecule for the preparation of a medicament for use in therapy, e.g. cancer or gene therapy, in which said photosensitizing agent and said transfer molecule are contacted (either separately, simultaneously or sequentially) with cells or tissues of a patient and said cells or tissues are irradiated with light of a wavelength effective to activate said photosensitizing agent. Methods of treatment comprising such methods form further aspects of the invention.

The photosensitizing agents of the invention may thus be used for transporting or transfecting any molecule into the cytosol of living cells either in vitro (i.e. in culture) or in vivo. These may be used not only to transfer molecules (or parts or fragments thereof) into the interior of a cell but also, in certain circumstances, to present or express them on the cell surface. Thus, following transport and release of a transfer molecule into the cell cytosol, if the cell(s) in question are specialised cells, such as for example antigen presenting cells, the molecule or fragment, may be transported to the surface of the cell where it may be presented on the outside of the cell, i.e. on the cell surface. Such methods have particular utility in the field of vaccination, where vaccine components, i.e. antigens or immunogens, may be introduced into a cell for presentation on the surface of that cell, in order to induce, facilitate or augment an immune response. Further details as to the utility of being able to express molecules on the cell surface are described in WO 00/54802.

The transfer molecules which can be introduced into the cytosol of cells using the photosensitizing agents of the present invention include molecules which do not readily penetrate cell membranes. Additionally, the agents herein described can increase the cytosol delivery and activity of molecules which are only partly able to penetrate the membrane of the cell or the membranes of intracellular vesicles. Transfer molecules may be organic compounds, proteins or fragments of proteins such as for example peptides, antibodies or antigens or fragments thereof. Another class of transfer molecules which may be introduced using the agents of the invention are cytotoxic drugs such as protein toxins or cytotoxic organic compounds. Molecules which may be of clinical interest for treatment of cancer, but are restricted by low or no uptake into the cytosol can be introduced into the cytosol and targeted to specific cells when using the methods herein described. Gelonin is an example of such a molecule.

Depending on the nature of the transfer molecule, the methods herein described may be used for treating various disorders, such as rheumatoid arthritis, artherosclerosis and other cardiovascular diseases, virus and other infections, psoriasis, solar keratosis, wound healing, fracture healing, warts and inherited genetic disorders such as cystic fibrosis, Gorlin's syndrome and ataxia telangiectasia.

Still another class of appropriate transfer molecules are nucleic acids. Nucleic acids may be used in the form of genes encoding for example therapeutic proteins, antisense RNA molecules, ribozymes, RNA aptamers or triplex forming oligonucleotides. Alternatively the nucleic acids may be employed in the form of non-encoding molecules such as for example synthetic DNA or RNA antisense molecules, ribozymes, aptamers, triplex forming oligonucleotides, peptide nucleic acids (PNAs), transcription factor "decoy" DNA or chimeric oligonucleotides for repair of specific mutations in the patient. Where appropriate the nucleic acid molecules may be in the form of whole genes or nucleic acid fragments optionally incorporated into a vector molecule e.g. a plasmid vector. The latter form has particular applicability when the transfer molecule is to be used in methods of gene therapy in which genes are therapeutically transferred to a patient's cells. This may be used in treating many diseases such as cancer, cardiovascular diseases, viral infections, and monogenic disorders such as cystic fibrosis.

Optionally, one or other or both of the photosensitizing agent and the transfer molecule to be introduced into the cells may be attached to or associated with or conjugated to carrier molecules, targeting molecules or vectors which can act to facilitate or increase the uptake of the photosensitizing agent or the transfer molecule or can act to target or deliver these entities to a particular cell type, tissue or intracellular compartment. Examples of carrier systems include polylysine or other polycations, dextran sulphate, different cationic lipids, liposomes, reconstituted LDL-particles or sterically stabilised liposomes. These carrier systems can generally improve the pharmacokinetics and increase the cellular uptake of the transfer molecule and/or the photosensitizing agent and may also direct the transfer molecule and/or the photosensitizing agent to intracellular compartments that are especially beneficial for obtaining photochemical internalization, but they do not generally have the ability to target the transfer molecule and/or the photosensitizing agent to specific cells (e.g. cancer cells) or tissues. However, to achieve such specific or selective targeting the carrier molecules, the transfer molecule and/or the photosensitizer may be associated with, bound or conjugated to specific targeting molecules that will promote the specific cellular uptake of the transfer molecule into desired cells or tissues. Such targeting molecules may also direct the transfer molecule to intracellular compartments that are especially beneficial for obtaining photochemical internalization.

Many different targeting molecules can be employed, e.g. as described in Curiel, D. T. (1999), Ann. New York Acad. Sci. 886, 158-171; Bilbao, G. et al. (1998), in Gene Therapy of Cancer (Walden et al., eds., Plenum Press, New York), Peng K. W. and Russell S. J. (1999), Curr. Opin. Biotechnol. 10, 454-457, Wickham T. J. (2000), Gene Ther. 7, 110-114.

The carrier molecule and/or the targeting molecule may be associated, bound or conjugated to the transfer molecule, to the photosensitizing agent or both, and the same or different carrier or targeting molecules may be used. Such targeting molecules or carriers may also be used to direct the transfer molecule to particular intracellular compartments especially beneficial for the employment of PCI, for example lysosomes or endosomes.

As mentioned above, the photosensitizing agents in accordance with the invention may also be used in photodynamic therapy, in particular photochemotherapy or diagnosis. Such methods are well documented in the patent and scientific literature, for example in WO 96/28412 and 98/30242.

When using the photosensitizers in PDT, the abnormalities and disorders which may be treated include any malignant, pre-malignant and non-malignant abnormalities or disorders responsive to photochemotherapy, e.g. tumours or other growths, skin disorders such as psoriasis or actinic keratoses and acne, skin abrasions, and other diseases or infections e.g. bacterial, viral or fungal infections, for example Herpes virus infections.

The internal and external body surfaces which may be treated using the compounds of the invention include the skin and all other epithelial and serosal surfaces, including for example mucosa, the linings of organs e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumours such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumors in solid tissues that can be made accessible to photoactivating light e.g. either directly, at time of surgery, or via an optical fibre inserted through a needle.

The compositions of the invention may be formulated in conventional manner with one or more physiologically acceptable carriers or excipients according to techniques well known in the art. The nature of the composition and carriers or excipient materials, dosages etc. may be selected in routine manner according to choice and the desired route of administration, purpose of treatment etc. Dosages may likewise be determined in routine manner and may depend upon the nature of the transfer molecule (where present), purpose of treatment, age of patient, mode of administration etc.

Compositions may be administered topically, orally or systemically. For use in PDT, topical compositions are preferred, and include gels, creams, ointments, sprays, lotions, salves, sticks, soaps, powders, pessaries, aerosols, drops, solutions and any of the other conventional pharmaceutical forms in the art. Topical administration to inaccessible sites may be achieved by techniques known in the art, e.g. by the use of catheters or other appropriate drug delivery systems.

Alternatively, the compositions may be provided in a form adapted for oral or parenteral administration, for example by intradermal, subcutaneous, intraperitoneal or intravenous injection. Alternative pharmaceutical forms thus include plain or coated tablets, capsules, suspensions and solutions containing the active component optionally together with one or more inert conventional carriers and/or diluents.

The concentration of the compounds as described hereinbefore in the compositions, depends upon the intended use of the compound, the nature of the composition, mode of administration, the condition to be treated and the patient and may be varied or adjusted according to choice. Generally however, for use in PDT, concentration ranges of the photosensitizer may be in the range of from 0.01 to 50%, e.g. 0.05 to 20%, e.g. 1-10% by weight. For use in PCI, it is important that the concentration of the photosensitizing agent is such that once taken up into the cell, e.g. into, or associated with, one or more of its intracellular compartments and activated by irradiation, one or more cell structures are disrupted, e.g. one or more intracellular compartments are lysed or disrupted. For example, photosensitizing agents may be used at a concentration of for example 10 to 50 µg/ml. For in vitro use the range can be much broader, e.g. 0.05-500 µg/ml. For in vivo human treatments the photosensitizing agent may be used in the range 0.05-20 mg/kg body weight when administered systemically or 0.1-20% in a solvent for topical application. When using the compounds herein described in PCI, the time of incubation of the cells with the photosensitizing agent (i.e. the "contact" time) can vary from a few minutes to several hours, e.g. even up to 48 hours or longer. The time of incubation should be such that the photosensitizing agent is taken up by the appropriate cells. The incubation of the cells with the photosensitizing agent may optionally be followed by a period of incubation with photosensitizer free medium before the cells are exposed to light and/or the transfer molecule is added.

Determining the appropriate doses of target molecules for use in accordance with the present invention is routine practice for a person skilled in the art. Where the transfer molecule is a protein or peptide, for in vitro applications the transfer molecules would generally be used at doses of less than 5 mg/ml (e.g 0.1-5 mg/ml) and for in vivo applications the transfer molecules would generally be used at doses of less than 5 mg/kg (e.g. 0.1-5 mg/kg). Where the transfer molecule is a nucleic acid, for in vitro applications an exemplary dose of the transfer molecules would be approximately 0.1-50 µg nucleic acid per $10^4$ cells and for in vivo applications approximately $10^{-6}$-1 g nucleic acid per injection in humans.

Following administration of a compound or composition as herein described (e.g. to a body surface), the area treated is exposed to light to achieve the desired effect, e.g. photochemical internalization or photochemotherapeutic effect. The light irradiation step to activate the photosensitizing agent may be effected according to techniques and procedures well known in the art. Suitable light sources capable of providing the desired wavelength and light intensity are well known in the art. The time for which the body surface or cells are exposed to light in the methods of the present invention may vary. For example, in PCI the efficiency of the internalization of the transfer molecule into the cytosol appears to increase with increased exposure to light. Generally, the length of time for the irradiation step is in the order of minutes to several hours, e.g. preferably up to 60 minutes e.g. from 1 to 30 minutes, e.g. from 0.5 to 3 minutes or from 1 to 5 minutes or from 1 to 10 minutes e.g. from 3 to 7 minutes, and preferably approximately 3 minutes, e.g. 2.5 to 3.5 minutes. Appropriate light doses can be selected by a person skilled in the art and will depend on the amount of photosensitizer accumulated in the target cells or tissues. The irradiation will in general be applied at a dose level of 40 to 200 Joules/cm$^2$, for example at 100 Joules/cm$^2$ at a fluence range of less than 200 mW/cm$^2$. Irradiation with wavelengths of light in the range 500-750 nm, e.g. 550 to 700 nm, is particularly suitable for in vivo use in the methods herein described.

In a yet further aspect the invention thus provides a method of photochemotherapeutic treatment of disorders or abnormalities of external or internal surfaces of the body, said method comprising administering to the affected surfaces a photosensitizing agent as herein described, e.g. a compound of formula I, or a pharmaceutically acceptable salt thereof, and exposing said surfaces to light, preferably to light in the wavelength region 300-800 nm, for example 500-700 nm.

Methods for irradiation of different areas of the body, e.g. by lamps or lasers are well known in the art (see for example Van den Bergh, Chemistry in Britain, May 1986 p. 430-439). For inaccessible regions this may conveniently be achieved using optical fibres.

The compounds of the invention may be formulated and/or administered with other photosensitizing agents, for example ALA or Photofrin®, or with other active components which may enhance the photochemotherapeutic effect. For example, chelating agents such as aminopolycarboxylic acids (e.g. EDTA), may be included in order to enhance accumulation of Pp and thus increase the photosensitizing effect. The chelating agent may conveniently be used at a concentration of 0.05 to 20% e.g. 0.1 to 10% by weight.

Surface-penetration assisting agents, in particular dialkylsuphoxides such as dimethylsulphoxide (DMSO) may also be used to enhance the photochemotherapeutic effect. The surface penetration agent may conveniently be provided in a concentration range of 0.2 to 50%, e.g. about 10% by weight.

According to the condition being treated, and the nature of the composition, the compounds for use in the invention may be co-administered with such other optional agents, for example in a single composition or they may be administered sequentially or separately. Indeed, in many cases a particularly beneficial photochemotherapeutic effect may be obtained by pre-treatment with the surface-penetration assisting agent in a separate step, prior to administration of the compounds for use in the invention.

Viewed from a further aspect, the invention thus provides a product comprising a photosensitizing agent as herein described, e.g. a compound of formula I, or a pharmaceutically acceptable salt thereof, together with at least one surface-penetration assisting agent, and optionally one or more chelating agents as a combined preparation for simultaneous, separate or sequential use in treating disorders or abnormalities of external or internal surfaces of the body which are responsive to photochemotherapy.

Alternatively viewed, this aspect of the invention also provides a kit for use in photochemotherapy of disorders or abnormalities of external or internal surfaces of the body comprising:

a) a first container containing a photosensitizing agent as herein described, e.g. a compound of formula I, or a pharmaceutically acceptable salt thereof, b) a second container containing at least one surface penetration assisting agent; and optionally c) one or more chelating agents contained either within said first container or in a third container.

It will be appreciated that the method of therapy using compounds as described hereinbefore inevitably involves the fluorescence of the disorder or abnormality to be treated. Whilst the intensity of this fluorescence may be used to eliminate abnormal cells, the localization of the fluorescence may be used to visualize the size, extent and situation of the abnormality or disorder.

The abnormality or disorder thus identified or confirmed at the site of investigation may then be treated through alternative therapeutic techniques e.g. surgical or chemical treatment, or by the method of therapy of the invention by continued build up of fluorescence or through further application of compounds of the invention at the appropriate site. It will be appreciated that diagnostic techniques may require lower levels of fluorescence for visualization than used in therapeutic treatments. Thus, generally, concentration ranges of 0.2 to 30% e.g. 1-5% (w/w) are suitable. Sites, methods and modes of administration have been considered before with regard to the therapeutic uses and are applicable also to diagnostic uses described here.

The compounds of the invention may also be used for in vitro diagnostic techniques, for example for examination of the cells contained in body fluids. The higher fluorescence associated with non-normal tissue may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, spinal fluid etc. Tissue samples or preparations may also be evaluated, for example biopsy tissue or bone marrow samples. The present invention thus extends to the use of compounds of the invention, or salts thereof for diagnosis according to the aforementioned methods for photochemotherapy, and products and kits for performing said diagnosis.

A further aspect of the invention relates to a method of in vitro diagnosis, of abnormalities or disorders by assaying a sample of body fluid or tissue of a patient, said method comprising at least the following steps:

i) admixing said body fluid or tissue with a photosensitizing agent as herein described, e.g. a compound of formula I, or a pharmaceutically acceptable salt thereof, ii) exposing said mixture to light, for example light having a wavelength in the range of 300-800 nm, iii) ascertaining the level of fluorescence, and iv) comparing the level of fluorescence to control levels.

The invention will now be described in more detail in the following non-limiting Examples, with reference to the accompanying Figures in which.

Figure 3:
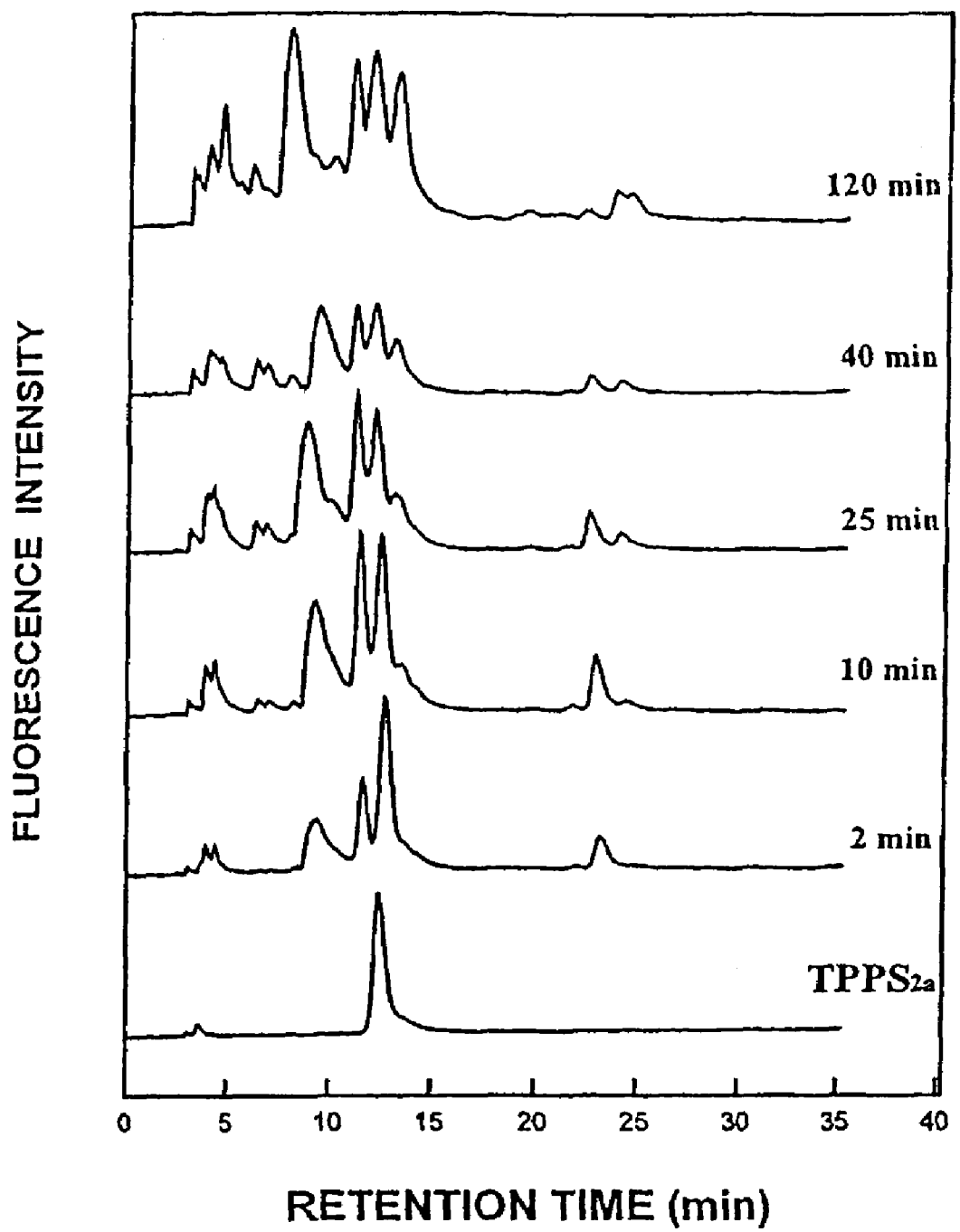
FIG. 3 shows HPLC-chromatographs of derivatives formed by exposure of $TPPS_{2a}$ to light. $TPPS_{2a}$ in the presence of TEA in benzene was exposed to non-monochromatic light and evaluated by reversed phase HPLC for the formation of fluorescent derivatives. The solution was exposed to light and samples isolated for measurement.
Figure 4:
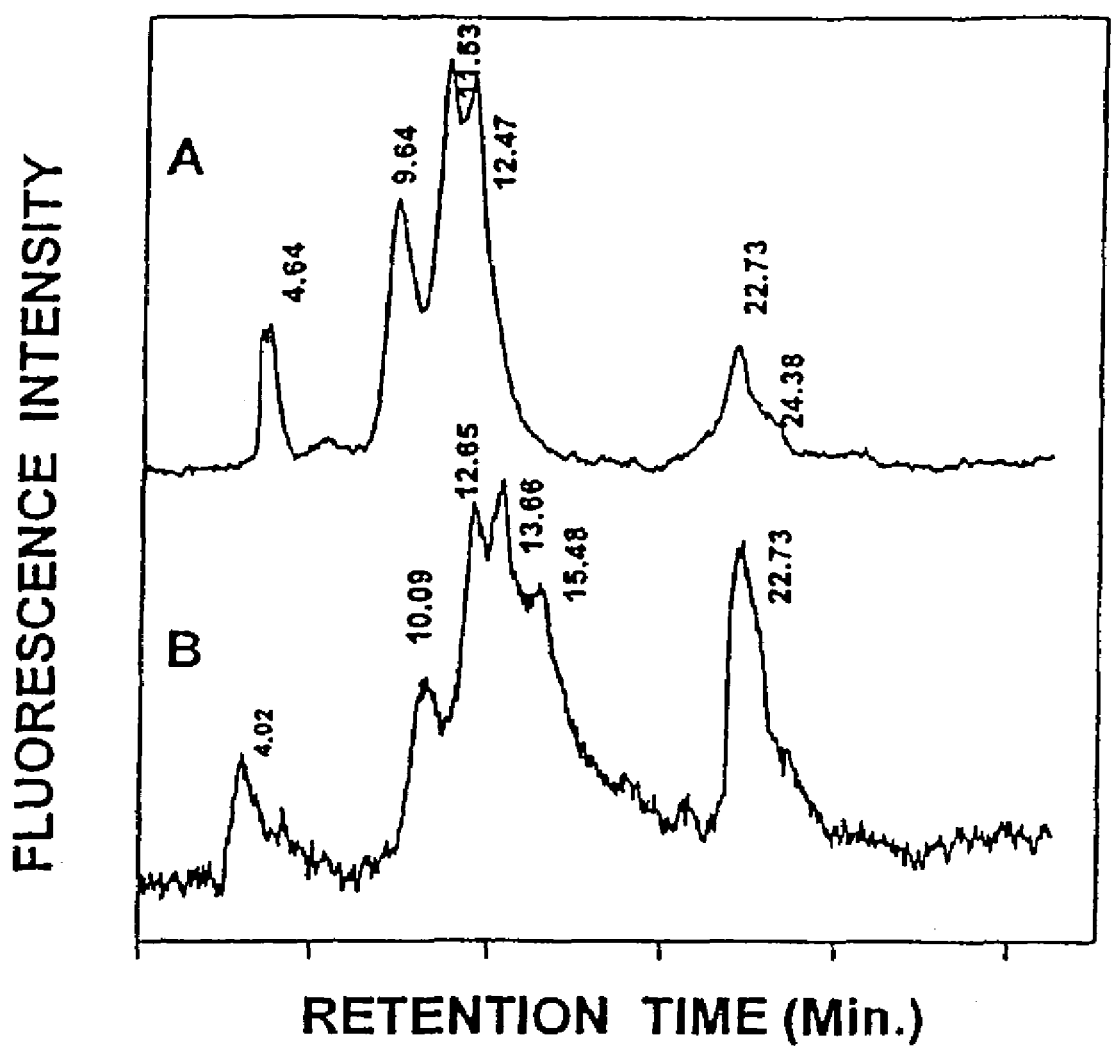

FIG. 4 shows HPLC-chromatographs of $TPCS_{2a}$ and cell extracts of V79 cells treated with $TPCS_{2a}$. V79 cells were treated with 1 µg/ml $TPCS_{2a}$ formed after 10 min of light exposure (a) according to FIG. 3. $TPCS_{2a}$ was extracted from the cells after 18 hours incubation and evaluated by HPLC (b). Peak retention times are indicated on the figure.

Figure 5:
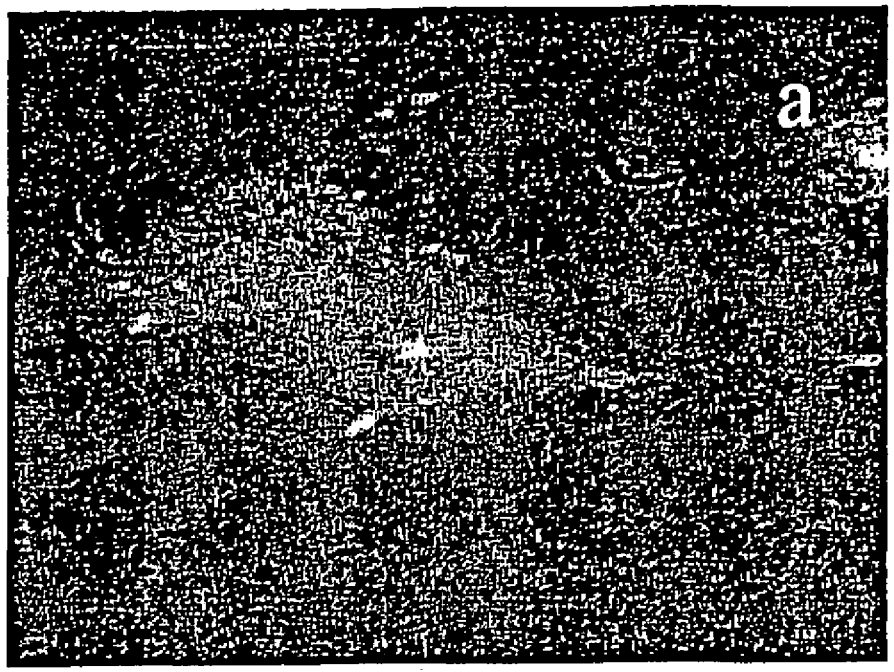
Figure 5:
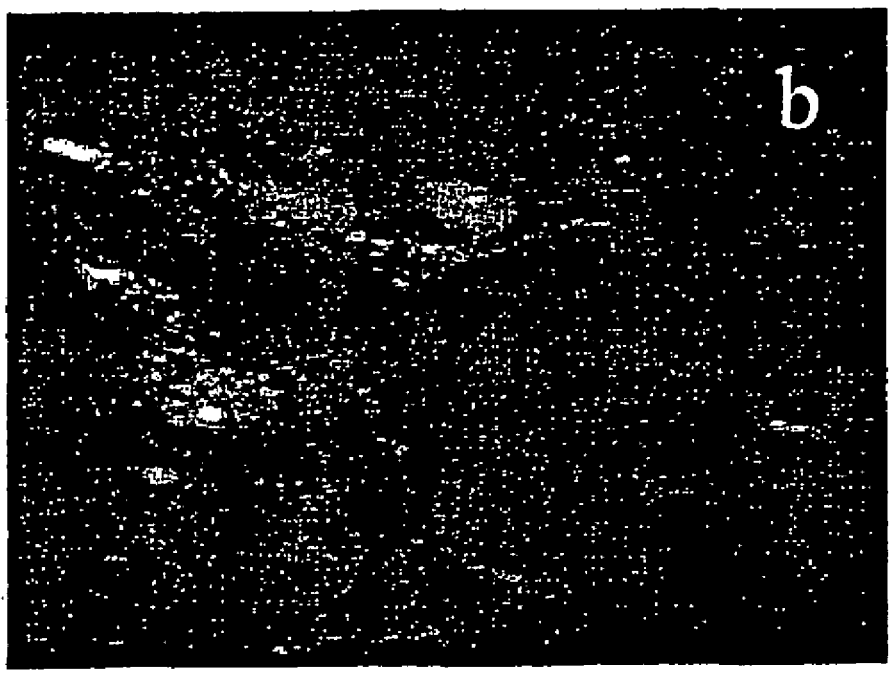

FIG. 5 shows fluorescence micrographs of V79 cells treated with $TPPS_{2a}$ and $TPCS_{2a}$. The cells were incubated with (a) 1 µg/ml $TPPS_{2a}$ or (b) 1 µg/ml $TPCS_{2a}$ for 18 hours followed by 1 hour incubation in sensitizer-free medium before microscopic evaluation.

Figure 6:
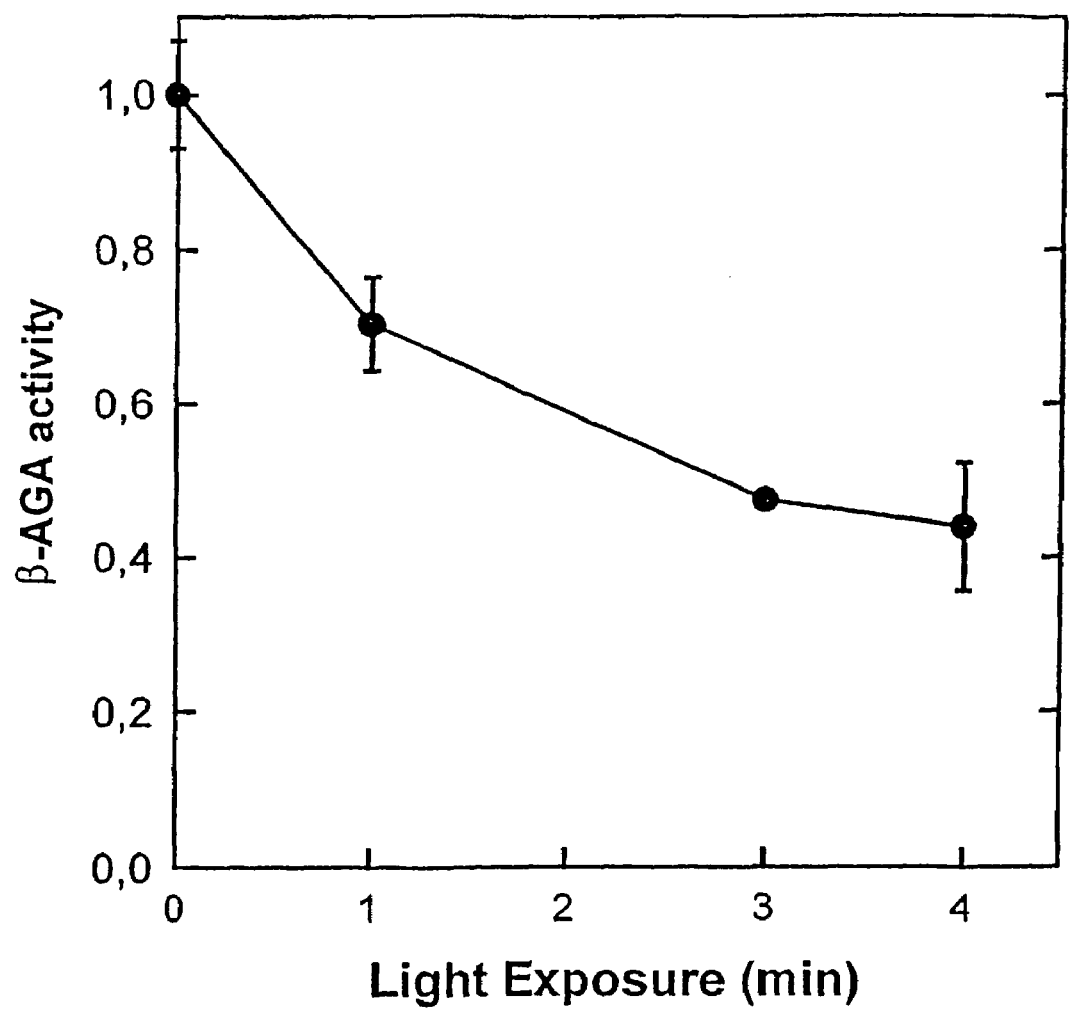

FIG. 6 shows fluence-response curves for inactivation of β-AGA activity in V79 cells exposed to 1 µg/ml $TPCS_{2a}$ for 18 hours followed by 1 hour incubation in sensitizer-free medium before exposure to red light.

Figure 7:
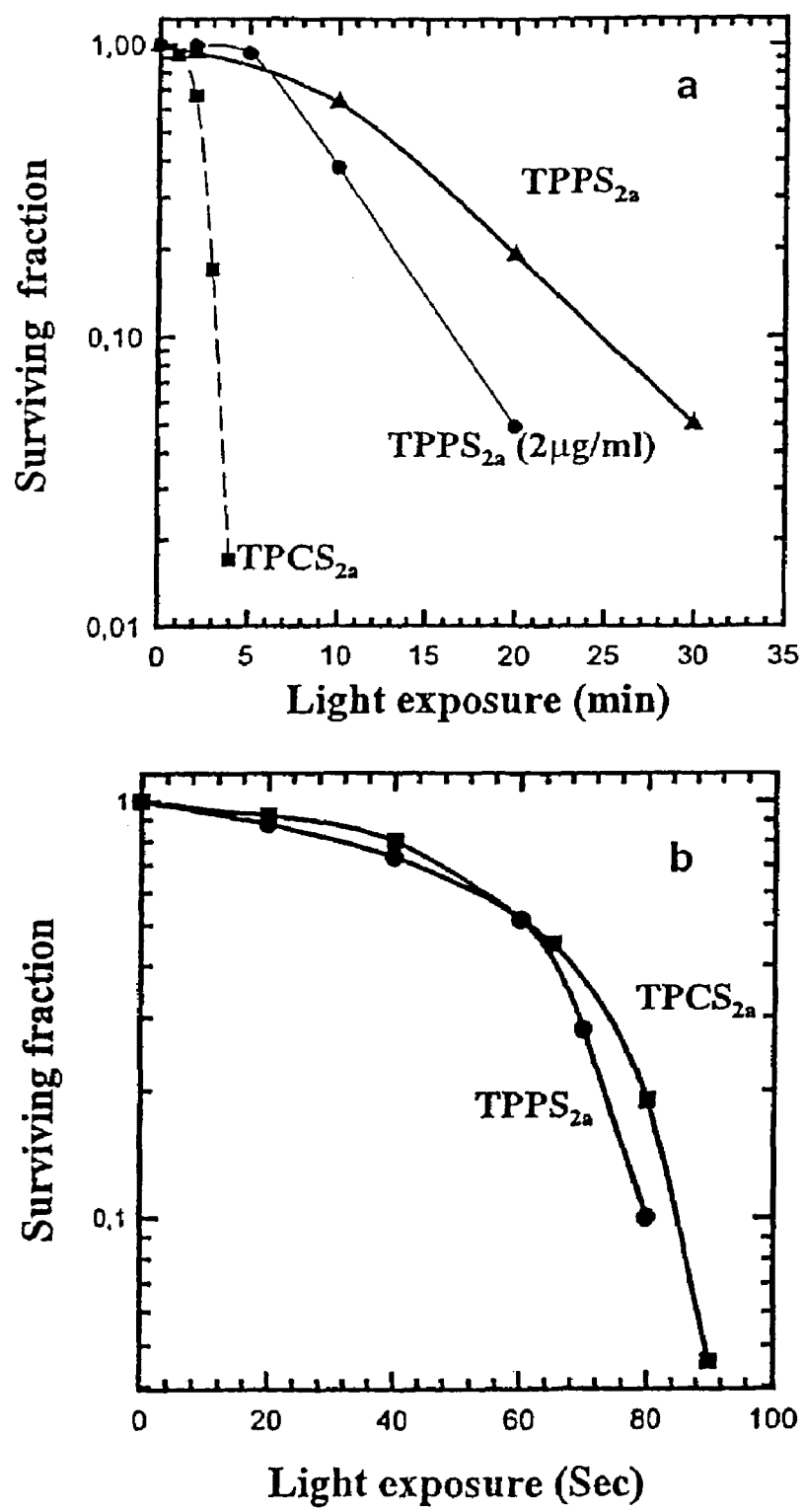

FIG. 7 shows dose-response curves for V79 cells incubated with $TPPS_{2a}$ and $TPCS_{2a}$ and exposed (a) to red light or (b) blue light. The cells were incubated with 1 or 2 µg/ml $TPPS_{2a}$ or 1 µg/ml $TPCS_{2a}$ for 18 hours followed by 1 hour incubation in sensitizer-free medium before exposure to light.

Figure 8:
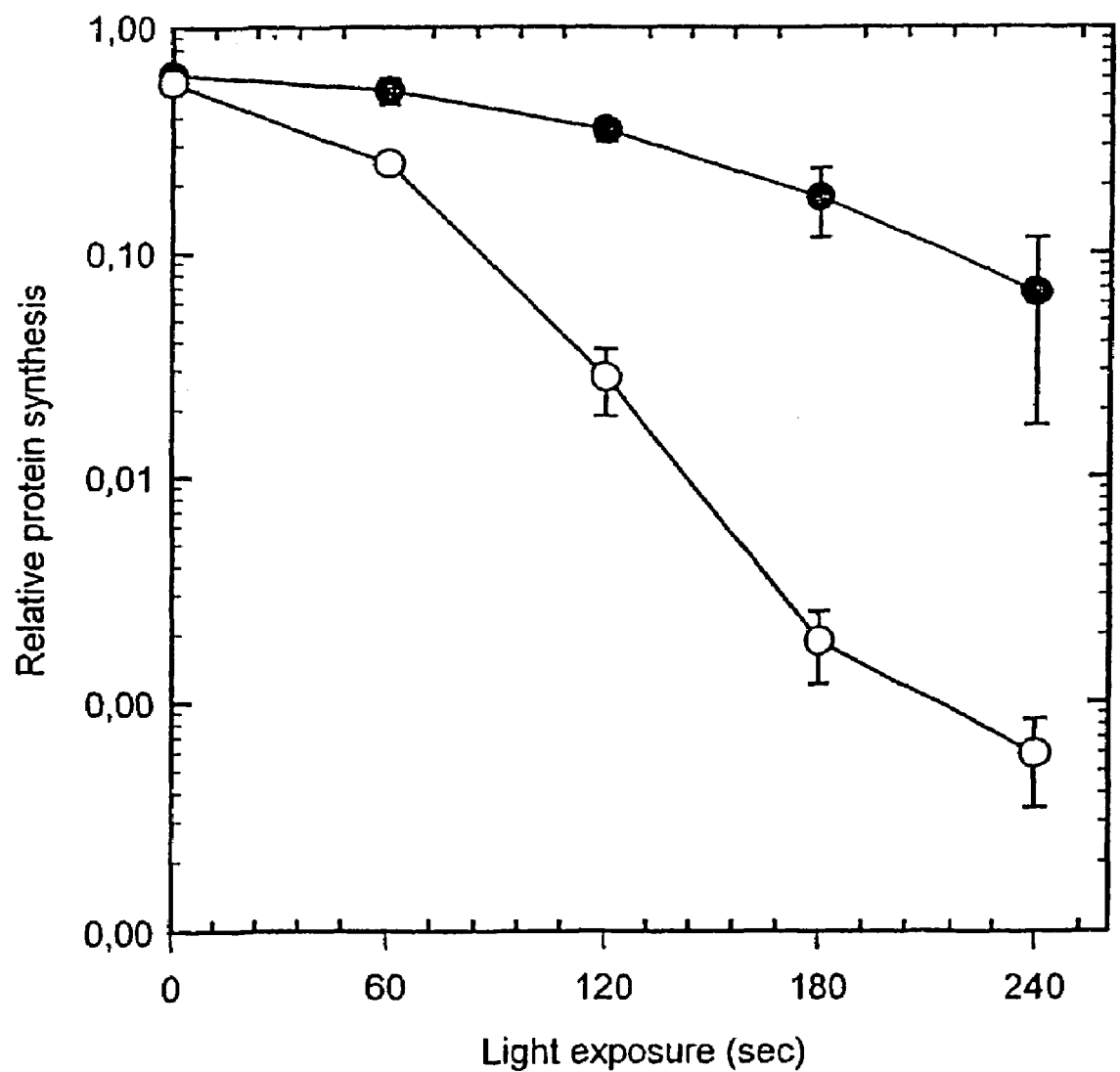

FIG. 8 shows protein synthesis after combined photochemical and gelonin treatments in V79 cells. The cells were treated with 1 µg/ml $TPCS_{2a}$ in the absence (filled circles) or presence (open circles) of 1 µg/ml gelonin and exposed to red light. Bars in this and preceding figures show the standard deviation from experiments performed in triplicate.

EXAMPLES

Materials and Methods

Materials

The photosensitizer $TPPS_{2a}$ was provided by Porphyrin Products (Logan, Utah, USA). Stock solution (2 mg/ml) of $TPPS_{2a}$ was dissolved in DMSO from Sigma (St. Louis, Mo., USA). Gelonin was purchased from Sigma. Toxin stock solution (2 mg/ml) was made by dissolving gelonin powder in PBS, pH 8.5 and kept at −20° C. until use. p-nitrophenyl-N-acetyl-D-glucosaminide was purchased from Sigma (St. Louis, Mo., USA).

Preparation of Tetraphenyl Chlorin Disulfonate—$TPCS_{2a}$

Tetraphenyl chlorin disulfonate ($TPCS_{2a}$) was prepared from $TPPS_{2a}$ essentially in accordance with the method described by Harel et al. (Photochem. Photobiol. 23: 337-341, 1976).

A mixture of 950 µl benzene/triethylamine (TEA) (18:7), 32 µl dimethyl sulfoxide (DMSO) and 18 µl $TPPS_{2a}$ (from a solution of 1 mg/ml in DMSO) was prepared and saturated with nitrogen for 5 min in a 1 ml cuvette. The mixture was then exposed to light from a 500 W high pressure Xenon lamp fitted to a Bausch and Lomb grating monochromator. The cuvette was exposed to 545±15 nm light at 15 W/m². The fluence rate was monitored by means of a UDT 11 A photodetector with a 223 radiometric filter. The absorption spectra was measured regularly by a Perkin-Elmer Lambda 15 UV/VIS spectrophotometer. The light pass was 1 cm.

For large scale production of $TPCS_{2a}$ (for cell studies) the mixture was made in a flask covered with plastic foil and continuously flushed with nitrogen during light exposure. The light path was kept smaller than 1 cm. The mixture was exposed to a bank of TL'/03 lamps and gently shaken during exposure to light. After irradiation the mixture was freeze dried and dissolved in DMSO.

Cell Cultivation

Cells of the established line V79 (ATCC CCL-93) derived from Chinese hamster lung fibroblasts were used. The cells were grown in MEM medium containing 10% foetal calf serum (FCS from Gibco, Paisley, UK), 100 U ml$^{-1}$ penicillin and 100 μg ml$^{-1}$ streptomycin (Gibco) at 37° C. in an incubator flushed with 5% $CO_2$ in air. The cells were subcultured twice a week.

Labeling with Photosensitizer

The cells were inoculated in 25 cm$^2$ flasks (Nunclon, Denmark) containing MEM medium with 10% FCS and left at 37° C. for 4-5 hours for proper attachment to the substratum. Subsequently, the cells were washed 3 times with medium and exposed to 1 μg/ml $TPPS_{2a}$ or $TPCS_{2a}$ in serum-containing medium for 18 hours. The cells were subsequently washed 3 times with the sensitizer-free medium and incubated for 1 hour before light exposure. The cells were then exposed to red light (Phillips TL 20 W/09) filtered through a Cinemoid 35 filter or blue light (Appl. Photophysics, Nood. 3026, London). The fluence rates reaching the cells were 1.35 mW/cm$^2$ and 1.5 mW/cm$^2$ from the red and the blue lamps respectively.

Toxicity Assays

Cell survival was measured by the colony-forming test as described by Berg et al. (Photochem. Photobiol. 53: 203-210, 1991). 1500 cells were inoculated in 25 cm$^2$ plastic tissue-culture flasks and treated with the photosensitizer and light as described above. After photochemical treatment the V79 cells were left for 5 days at 37° C. in serum-containing culture medium to allow for formation of countable colonies. The cells were then fixed in ethanol, stained with methylene blue and the colonies counted. Inhibition of protein synthesis was assessed by [$^3$H]-leucine incorporation into proteins, measured at 24 hours post light exposure as described by Llorente et al. (FEBS Lett. 431: 200-204, 1998).

HPLC

The porphyrins were extracted from the cells by scraping the cells in acidified methanol (5 μl concentrated HCl in 10 ml of methanol) as described by Berg et al. (Br. J. Cancer 74: 688-697, 1996). The cell debris was pelleted and the supernatant collected. The porphyrins were concentrated by flushing the extracts with $N_2$ until the volume was reduced to approximately 150-200 μl and additionally precipitated proteins were pelleted. 100 μl of the supernatant was mixed with 235 μl of 10 mM $Na_2PO_4$, pH adjusted to approx. 10.5 by means of 5 M KOH, and directly used for HPLC analysis. The porphyrins were quantitatively extracted from the cells by this procedure. Stock solutions of photosensitizers were diluted directly in the start buffer.

The HPLC system consisted of a pump (Spectra Physics 8800), a reversed phase column (Supelcosil LC-18-T (4.6× 250 mm), Supelco, S. A., Gland, Switzerland), a fluorescence detector (LDC fluoromonitor III) and an integrator (Spectra Physics Data-jet) connected to a computer. Solvent A was a mixture of methanol and water (30:70 by volume) containing 1.5 mM phosphate, adjusted to pH 7.0. Solvent B was a mixture of methanol and water (95:5 by volume) containing 1.5 mM phosphate, adjusted to pH 7.5. A 30 min linear gradient between 40 and 20% of solvent A was applied followed by 5 min linear gradient to 100% of solvent B. The fluorescence was detected by excitation in the wavelength region 330-400 nm. Scattered light was eliminated from the fluorescence by means of a cut-off filter transmitting only light with a wavelength longer than 410 nm.

Fluorescence Microscopy 28 cm$^2$ dishes (Falcon 3002, Becton Dickinson, Plymouth, UK) were used in the microscopical studies. The cells were washed once with PBS and a cover glass was gently put on top of the PBS layer. The cells were subsequently studied by a Zeiss Axioplan microscope (Zeiss, Obercochen, Germany) equipped with epifluorescence. A HBO/100 W mercury lamp was used for excitation. The cells and the cellular fluorescence were studied by means of a cooled charge-coupled device (CCD) camera (TE2, Astromed, Cambridge, UK). A computer controlled the camera operation and was used for digital image processing and storage. The microscope was equipped with a 390-440 nm band pass excitation filter, a 470 nm dichroic beam splitter and a 610 nm long pass filter.

Enzyme Assay

The photochemical inactivation of the lysosomal enzyme β-AGA was measured as described by Beaufay et al. (J. Cell Biol. 61: 188-200, 1974). The method is based on the formation of p-nitrophenol (from the substrate p-nitrophenyl-N-acetyl-D-glucosaminide) which can be measured spectrophotometrically at 420 nm. The cells were isolated immediately after exposure to light and prepared for enzymatic analysis.

Example 1

Photochemical Reduction of $TPPS_{2a}$

In accordance with the method described by Harel et al. (Photochem. Photobiol. 23: 337-341, 1976), $TPPS_{2a}$ was exposed to light in a solution of triethylamine (TEA) in benzene saturated with nitrogen. The solution was exposed to light of 545 nm in a cuvette as described above in "Materials and Methods".

Figure 1:
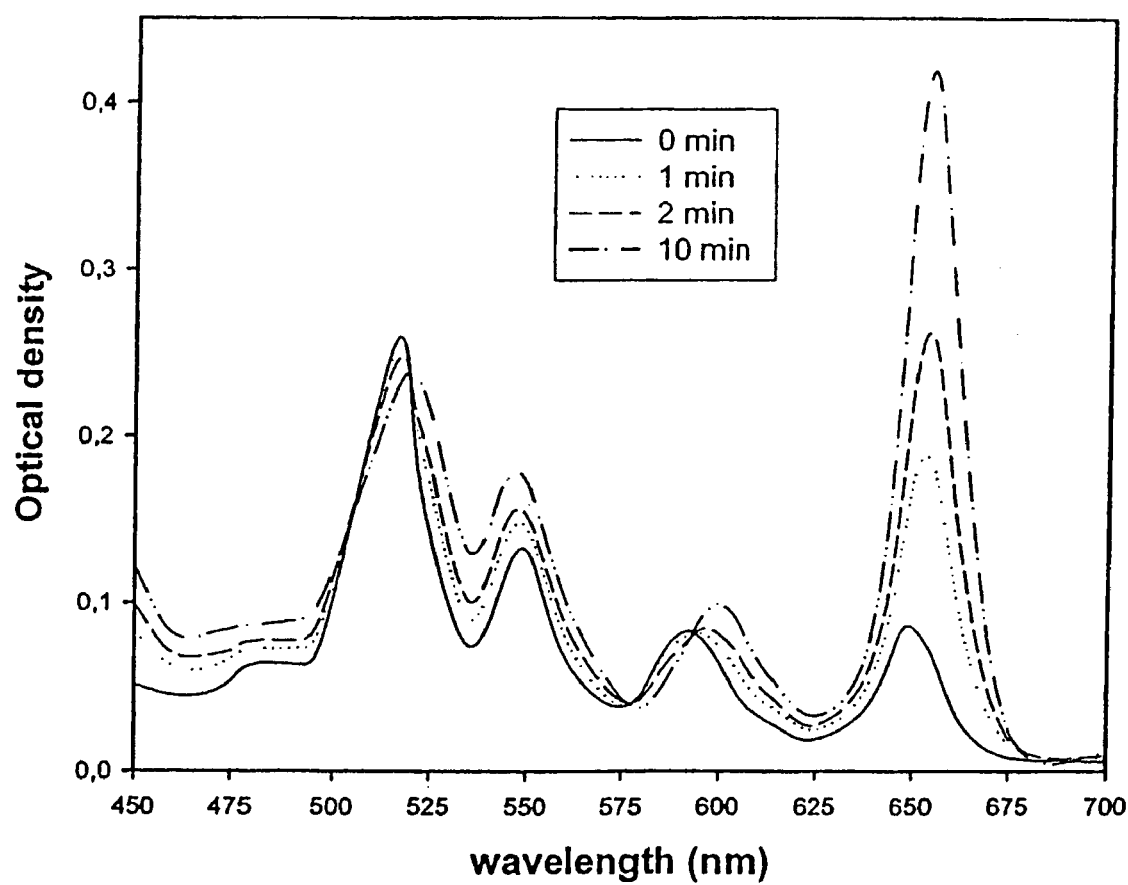
FIG. 1 shows the absorption spectra of $TPPS_{2a}$ in the presence of triethylamine (TEA) in benzene both prior to and after exposure to monochromatic light for various periods of time.
Figure 2:
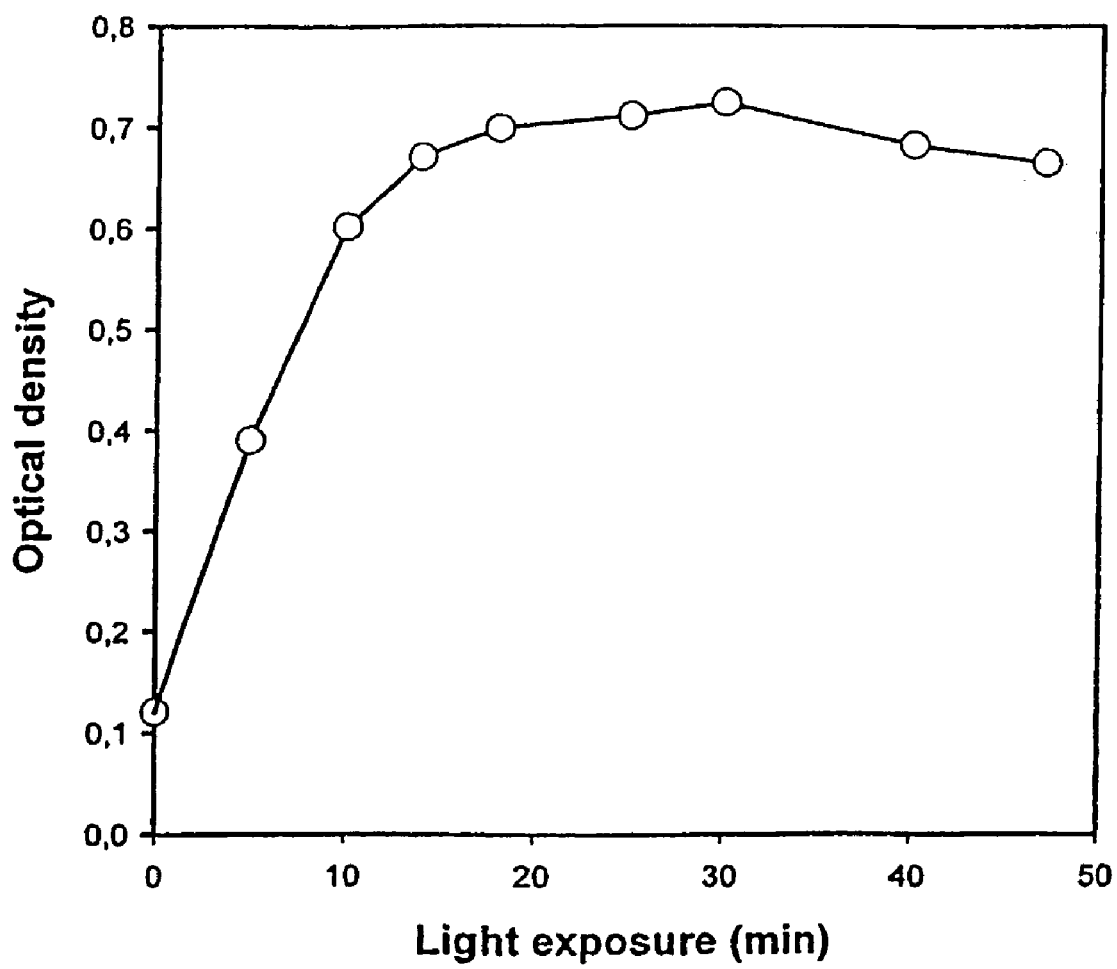
FIG. 2 is a graph showing the effect of light exposure on the maximum optical density of the 646-655 nm peak of $TPPS_{2a}$. The solution containing $TPPS_{2a}$ in the presence of TEA in benzene was exposed to monochromatic light and the optical density measured.

FIG. 1 shows the change in absorption spectrum upon exposure to light and a spectrum for the final product which is characteristic of chlorins. The peak of band I of the Q-bands shifted from 646 nm to 655 nm and increased in intensity 5.8-fold at the maximum (FIG. 2). Isobestic points were observed at 593 nm as well as at 505 nm, 518 nm and 577 nm. The absorption bands after irradiation are characteristic of chlorins.

In order to scale up the production of the chlorin for cell studies, larger volumes of $TPPS_{2a}$ solutions were exposed to light and prepared as described in "Materials and Methods". The time scale for the increase in the 655 nm absorption peak was similar to that as described above and shown in FIG. 2. Formation of the chlorin was followed by HPLC as shown in FIG. 3 which shows that several isomers of the chlorin were formed. Solutions exposed to 10 min of light were used further for treatment of cells in culture. About 23% of the product after 10 min of irradiation had a similar retention time to $TPPS_{2a}$, but the peak showed a typical chlorin absorption spectrum.

Example 2

Photobiological Evaluation of $TPCS_{2a}$

Chinese hamster lung fibroblasts of the cell line V79 were used for biological evaluations of the photochemical effects of the chlorin, $TPCS_{2a}$. The cells were incubated overnight with the chlorin, the photosensitizer extracted from the cells and the extracts evaluated by HPLC. As seen in FIG. 4 the pattern of fluorescent peaks in the cell extracts was similar to that from the stock solution. A reverse phase C-18 column was used for the chromatography where in general the retention time increases with the hydrophobicity of the compounds. Cellular uptake of the chlorin was found to increase with the hydrophobicity of the isomers.

The photosensitizer $TPPS_{2a}$ has previously been found to localize in endocytic vesicles of cells incubated with this compound (Berg et al. Photochem. Photobiol. 52: 481-487, 1990). The intracellular localization of $TPCS_{2a}$ was found to be similar to that of $TPPS_{2a}$, indicating that $TPCS_{2a}$ also localizes in endocytic vesicles (see FIG. 5). This was further demonstrated by the photochemical inactivation of the lysosomal enzyme β-N-acetyl-glucosaminidase (see FIG. 6). Thus, by comparing the intracellular fluorescence pattern of the lysosomal localizing photosensitizer $TPPS_{2a}$, $TPCS_{2a}$ was shown indirectly to localize in endocytic vesicles of V79 cells by fluorescence microscopy and directly by measurements of photochemical inactivation of the lysosomal enzyme 13-AGA.

The benefit of using a chlorin instead of a porphyrin in photodynamic therapy is the higher extinction coefficient of the chlorin in the red wavelength area. This was clearly demonstrated by comparing exposure of cells treated with $TPPS_{2a}$ and $TPCS_{2a}$ to blue and red light (see FIG. 7). In FIG. 7b it is seen that cells treated with $TPPS_{2a}$ or $TPCS_{2a}$ were equally sensitive to blue light while the cells treated with $TPCS_{2a}$ were about 6 times more sensitive to red light than the cells treated with the porphyrin, $TPPS_{2a}$ (FIG. 7a)

Intracellular localization of $TPCS_{2a}$ in endocytic vesicles and thus its possible use in the photochemical internalization (PCI) of macromolecules was evaluated by internalization of the type I ribosome-inactivating protein toxin gelonin. Gelonin has been found to exert low toxicity alone or in combination with light (Berg et al. Cancer Res. 59: 1180-1183, 1999). The protein synthesis was reduced by about 10% in cells treated with 1 µg/ml gelonin for 18 hours. However, as shown in FIG. 8 $TPCS_{2a}$ and light strongly potentiate the cytotoxicity of gelonin as measured by protein synthesis 24 hours after exposure to light. There was a slight (20%) reduction in protein synthesis induced by $TPCS_{2a}$ alone which was not observed in the clonogenicity assay. The results demonstrate that gelonin is internalized into the cells following photochemical treatment with $TPCS_{2a}$.

Discussion

The present study shows that a disulfonated tetraphenylporphine can be reduced to its chlorin form by photochemical reduction in the presence of TEA under anaerobic conditions. The photochemical reduction leads to a 5.8-fold increase in the extinction coefficient of band I of the Q-bands caused by formation of several chlorin isomers. When compared to the parent porphyrin, $TPPS_{2a}$, the photosensitizing ability of the chlorin $TPCS_{2a}$ in V79 cells was found to be equally efficient in sensitizing cells to photoinactivation with blue light and 6-fold more efficient with red light.

$TPCS_{2a}$ was shown indirectly to localize in endocytic vesicles of V79 cells by fluorescence microscopy. This was confirmed directly by measurements of photochemical inactivation of the lysosomal enzyme β-AGA. The rate of β-AGA inactivation relative to cell survival was found to be similar to that previously found for $TPPS_{2a}$ (Berg et al., Int. J. Cancer 59: 814-822, 1994) indicating a similar distribution of these compounds between the membranes of the endocytic vesicles and their lumen.

It was also shown that $TPCS_{2a}$ may be utilized as a photosensitizer for photochemical internalization (PCI) of macromolecules, as demonstrated by the PCI of gelonin.

The invention claimed is:

1. A compound which comprises a sulphonated meso-tetraphenyl chlorin of formula I, an isomeric form of formula I, or a pharmaceutically acceptable salt thereof:

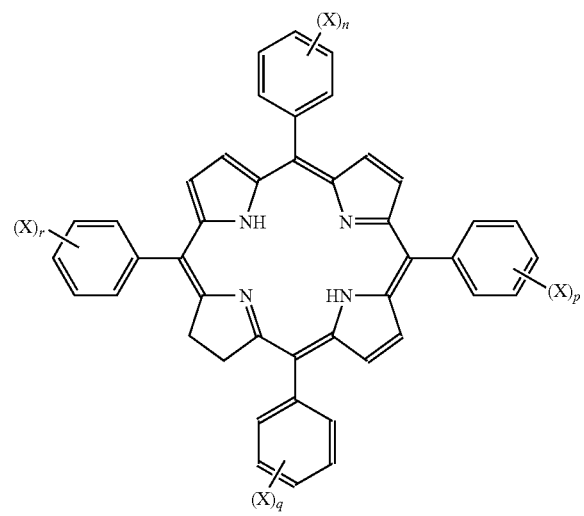

(I)

wherein
X is $SO_3H$;
n, p, q, and r are each independently 0 or 1; and
the sum of n, p, q, and r is 2.

2. A compound as claimed in claim 1, wherein the sum of n, p, q and r is 2 and each group X is present at the same ring position within each phenyl ring.

3. A compound as claimed in claim 2, wherein said ring position is the meta- or para-position.

4. A compound as claimed in claim 1, wherein the sum of n, p, q and r is 2 and the substituted phenyl rings are situated adjacent to the reduced pyrrole ring.

5. A compound as claimed in claim 1, wherein said chlorin is a compound of formula (II):

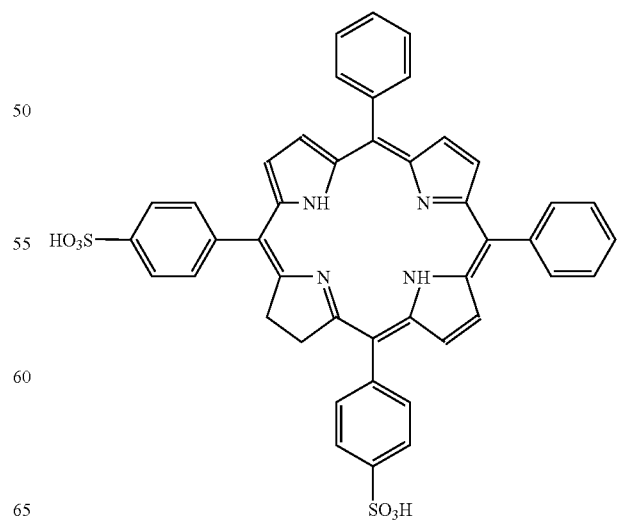

II an isomer, or a pharmaceutically acceptable salt of any one of the foregoing.

6. A compound obtainable by reducing one double bond in the porphyrin macrocycle of a sulphonated meso-tetraphenyl porphyrin of formula III, an isomeric form of formula III, or a pharmaceutically acceptable salt thereof:

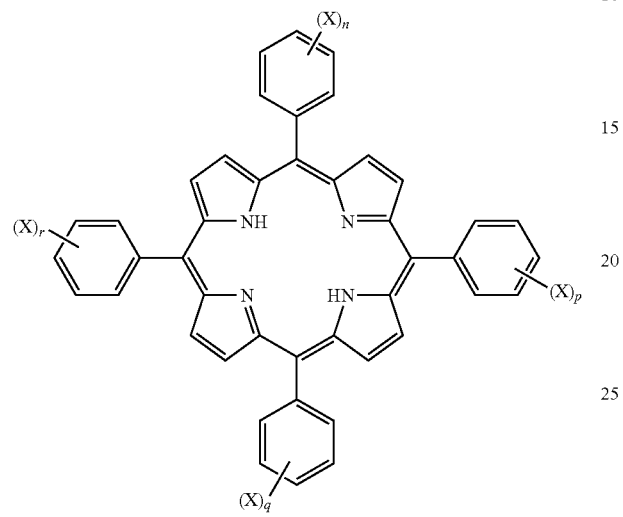

wherein
X is $SO_3H$;
n, p, q, and r are each independently 0 or 1; and
the sum of n, p, q, and r is 2.

7. A compound as claimed in claim 6, wherein said porphyrin is $TPPS_{2a}$ (Tetraphenyl porphine disulfonate).

8. A pharmaceutical composition comprising a photosensitizing agent together with at least one pharmaceutical carrier or excipient, wherein the photosensitizing agent comprises a sulphonated meso-tetraphenyl chlorin of formula I, an isomeric form of formula I, or a pharmaceutically acceptable salt thereof:

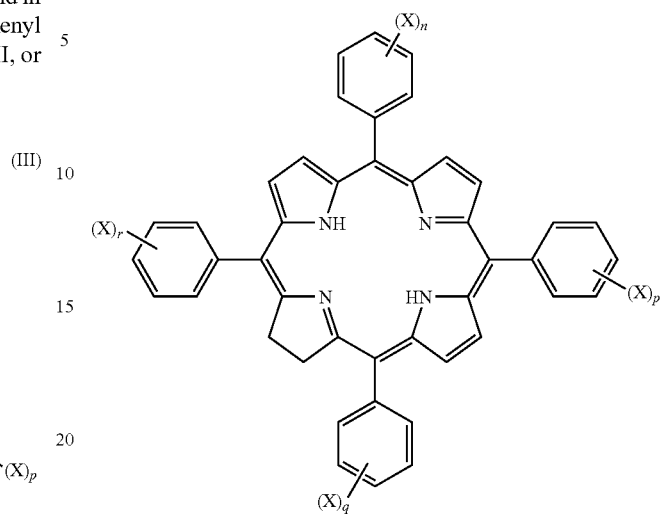

wherein
X is $SO_3H$;
n, p, q, and r are each independently 0 or 1; and
the sum of n, p, q, and r is an integer from 1 to 4.

9. A process for preparing a photosensitizing agent as defined in claim 1, said process comprising at least one of the following steps:
(a) reducing a sulphonated meso-tetraphenyl porphyrin or an iron chelate complex thereof;
(b) if desired, separating the mixture of compounds formed in step (a); and
(c) converting a compound formed in step (a) or step (b) into a pharmaceutically acceptable salt thereof.

10. A method for introducing a transfer molecule into the cytosol of a cell, said method comprising:
(a) contacting said cell with a photosensitizing agent as claimed in claim 1, or a pharmaceutically acceptable salt thereof;
(b) contacting said cell with said transfer molecule; and
(c) irradiating said cell with light of a wavelength effective to activate the photosensitizing agent.

* * * * *